United States Patent [19]

Dorawala et al.

[11] 4,215,018

[45] Jul. 29, 1980

[54] STEAM DEALKYLATION CATALYST AND A METHOD FOR ITS ACTIVATION

[75] Inventors: Tansukhlal G. Dorawala, Wappingers Falls; Russell R. Reinhard, Hopewell Junction, both of N.Y.

[73] Assignee: Texaco Inc., White Plains, N.Y.

[21] Appl. No.: 939,512

[22] Filed: Sep. 5, 1978

Related U.S. Application Data

[60] Division of Ser. No. 850,120, Nov. 10, 1977, Pat. No. 4,136,129, which is a continuation of Ser. No. 610,806, Sep. 5, 1975, abandoned.

[51] Int. Cl.$^2$ .................... B01J 21/04; B01J 23/78
[52] U.S. Cl. .................... 252/466 J; 252/474
[58] Field of Search .................... 252/466 J, 474

[56] References Cited

U.S. PATENT DOCUMENTS

| | | | |
|---|---|---|---|
| 2,960,545 | 11/1960 | Seubold | 260/672 R |
| 3,649,706 | 3/1972 | Lester | 260/672 R |
| 3,812,196 | 5/1974 | Uchiyama et al. | 260/672 R |

*Primary Examiner*—W. J. Shine
*Attorney, Agent, or Firm*—Carl G. Ries; Robert A. Kulason; Carl G. Seutter

[57] ABSTRACT

Alkylaromatic hydrocarbons are dealkylated in the presence of a catalyst typically containing oxides of nickel, potassium, and aluminum.

12 Claims, No Drawings

STEAM DEALKYLATION CATALYST AND A METHOD FOR ITS ACTIVATION

This is a division of application Ser. No. 850,120, filed Nov. 10, 1977, now U.S. Pat. No. 4,136,129, which is a continuation of Ser. No. 610,806, filed Sept. 5, 1975, now abandoned.

FIELD OF THE INVENTION

This invention relates to the conversion of hydrocarbons. More particularly, it relates to the dealkylation of alkylaromatic hydrocarbons such as toluene.

BACKGROUND OF THE INVENTION

Steam demethylation may be carried out by passing an alkylaromatic hydrocarbon, typically toluene, together with steam through a furnace to yield a product containing principally benzene. Steam dealkylation is carried out in the presence of catalysts; and typical catalyst compositions may include zeolites or amorphous inorganic oxides such as silica, alumina, silica-alumina magnesia, zirconia, etc. commonly bearing metal oxides. It is found that such processes are less than fully satisfactory because of low yields of product, degradation of catalyst, poor product selectivity etc.

It is an object of this invention to provide a steam dealkylation process particularly characterized by use of a rugged catalyst. Other objects will be apparent to those skilled in the art.

STATEMENT OF THE INVENTION

In accordance with certain of its aspects, the novel process of this invention for dealkylating an alkylaromatic hydrocarbon charge may comprise passing a mixture of steam and an alkylaromatic hydrocarbon, at steam dealkylating conditions, into contact with an activated supported catalyst comprising oxides of (i) a Group VIII metal and (ii) a Group IA metal—thereby forming a product gas containing dealkylated alkylaromatic hydrocarbon; and recovering said product gas containing dealkylated alkylaromatic hydrocarbon.

DESCRIPTION OF THE INVENTION

In accordance with certain of its aspects, the charge alkylaromatic hydrocarbon which may be treated by the process of this invention may be a stream typically having a boiling point of 176° F.-1292° F. (80° C.-700° C.). The stream may contain alkylaromatic hydrocarbons, either pure or in admixture, in varying quantities. This charge stream may typically contain toluene, xylenes, ethyl benzenes, propyl benzenes etc. The preferred charge hydrocarbon contains toluene; and in the preferred embodiment, it may be substantially entirely toluene se.

Typical charge streams which may be treated by the process of this invention may include aromatic extracts or reformate streams containing alkylaromatic hydrocarbons. Illustrative of such charge streams may be a reformate commonly containing the following components (% by volume);

TABLE

| Component | Broad | Typical |
|---|---|---|
| Paraffins | 30–45 | 40 |
| Olefins | 0–2 | 1 |
| Naphthenes | 1–5 | 3 |
| Aromatics | 45–65 | 56 |

Of the aromatic content of the reformate, 80%–100%, typically 90% may be present as alkylaromatic hydrocarbons.

This reformate may have a (RON Clear) octane number of 90, an IBP of 115° F., an EBP of 410° F., and an API gravity of 47.7.

Particularly desirable results may be achieved by use, as the hydrocarbon charge, of compositions containing substantial proportions of toluene.

The supported catalyst which may be employed in practice of the process of this invention may comprise oxides of (i) a Group VIII metal and (ii) a Group I A metal.

The Group VIII metal may include iron Fe, Cobalt Co, nickel Ni, ruthenium Ru, rhodium Rh, palladium Pd, osmium Os, iridium Ir, and platinum Pt. Preferably the Group VIII metal may be nickel or cobalt; and in the most preferred embodiment, it is nickel.

The Group I A metal, an alkali metal, may be lithium Li, sodium Na, potassium K, rubidium Rb, or cesium Cs. In the preferred embodiment, it is potassim K.

The catalyst support may be active or inactive or inert. Typically the support may be a clay, a silica, a metal oxide, a zeolite, etc. The preferred porous materials may include alumina, silica, silica-alumina, silica-magnesia, silica-titania, silica-beryllia, silica-zirconia, silica-alumina-magnesia, etc. The preferred support is an inert support such as slumina, preferably gamma-alumina.

In typical practice of the process of this invention, the catalyst composition may contain the following components in the indicated parts by weight (expressed as oxide):

TABLE

| Component | Broad | Preferred | Typical |
|---|---|---|---|
| Group VIII | 0.5–40 | 0.5–20 | 15 |
| Fe-Co-Ni | 6–40 | 6–20 | 15 |
| or | | | |
| Ru-Rh-Pd Os-Ir-Pt | 0.5–10 | 0.5–5 | 1 |
| Group I A | 0.01–5 | 1–4 | 2 |
| Support | 55–99.5 | 76–98.5 | 83 |

The preferred catalyst may be that containing nickel-potassium-aluminum; and the catalyst composition may contain the following (expressed as oxide):

TABLE

| Component | Broad | Preferred | Typical |
|---|---|---|---|
| Ni | 6–40 | 6–20 | 15 |
| K | 0.01–5 | 1–4 | 2 |
| Al | 55–94 | 76–93 | 83 |

An alternative composition containing a noble Group VIII metal may be as follows (expressed as oxide):

TABLE

| Component | Broad | Preferred | Typical |
|---|---|---|---|
| Pt | 0.5–10 | 0.5–5 | 1 |
| K | 0.01–5 | 1–4 | 2 |
| Al | 85–99.5 | 91–98.5 | 97 |

In terms of molar proportions, the catalyst may be represented by the formula:

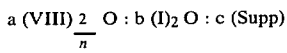

wherein (VIII) represents a metal of Group VIII of the Periodic Table having a valence n, (I) represents a metal of Group I A of the Periodic Table. a. may be 0.002–0.75, preferably 0.002–0.38, say 0.20; b may be 0.00003–0.17, preferably 0.003–0.13, say 0.02; and c may be 0.15–2.49, preferably 0.75–2.46, say 0.81.

In the preferred embodiment, the catalyst may be represented by the formula

wherein a is 0.08–0.54, preferably 0.08–0.27, say 0.20; b is 0.01–0.05, preferably 0.01–0.04, say 0.02; and c is 0.15–0.93 preferably 0.75–0.91, say 0.81.

A preferred catalyst may consist essentially of Group VIII metal oxide and Group I A metal oxide on support.

In practice of this invention, the catalyst may be prepared by immersing a catalyst support in a solution containing the metal ions. The support, typically a gamma-alumina extrudate of 1.5 mm diameter and 10 mm length may first be steam sintered at 900°–1400° F., say 1110° F. for 5–25 hours, say 12 hours. During sintering, there may be passed through the bed air at VHSV (STP) of 40–600, say 230 together with steam at water VHSV of 0.05–0.10, say 0.06. The steamed alumina is then calcined for 1–5, say 2 hours at 900° F.–1200° F., say 1000° F. The initial surface of the alumina, typically 200–400, say 231 meter $^2$/gram may be decreased to 70%–95%, say about 80% to a value of 140–380, say 192 meter $^2$/gram.

The support (166 parts), preferably as so treated, is cooled to 32° F.–80° F., say about 32° F. and wetted with 27–777 parts, say 257 parts of solution prepared by dissolving soluble decomposable salts of metals of Group VIII and Group I A in aqueous solution. Preferably 2–300 parts, more preferably 75–200, say 148.5 parts of salt of Group VIII metal, typically nickel nitrate hexahydrate Ni $(NO_3)_2.6H_2O$ and 0.09–43 parts, preferably 0.9–34, say 8.6 parts of salt of Group I A metal, typically potassium nitrate are dissolved in 25–400 parts, say 100 parts of water to yield total solution in amount of 27–777 parts, say 257 parts. (Although nitrates of the metals are preferably employed, acetates, formates, citrates, or other soluble, decomposable salts may be used).

The solution is poured over the support and is stirred intermittently for 0.5–10 hours, say 1 hour and the solution (25–2400 parts, typically 50 parts) may then be decanted. The impregnated support is dried at 212° F.–400° F., say 300° F., then heated to decomposition temperature of typically 650° F.–1000° F., say 700° F., and calcined for 1–10 hours, say 2 hours at 650° F.–1400° F., say 700° F. This procedure is preferably related 2–4, preferably 2 times more until all the metal salt solution is absorbed by the support. The composition so prepared in amount of 167–259 parts, say 208 parts may be characterized by the formula a (VIII) $\frac{2}{n}$ O : b (I)$_2$ O : c (Supp)

wherein all the symbols are as noted supra.

Preferred catalyst compositions may have the formulas:

| | | |
|---|---|---|
| 0.20 NiO | : 0.02 K$_2$O | : 0.81 Al$_2$O$_3$ |
| 0.10 NiO | : 0.01 K$_2$O | : 0.90 Al$_2$O$_3$ |
| 0.20 NiO | : 0.05 Na$_2$O | : 0.81 Al$_2$O$_3$ |
| 0.20 CoO | : 0.02 K$_2$O | : 0.81 Al$_2$O$_3$ |
| 0.20 CoO | : 0.03 Na$_2$O | : 0.81 Al$_2$O$_3$ |
| 0.108 NiO | : 0.01 K$_2$O | : 1.54 SiO$_2$ |
| 0.20 CoO | : 0.02 K$_2$O | : 2.06 MgO |

It should be noted that calcination of the catalyst when it contains nickel should be not at temperature above about 700° F. Preferably if there are other components present (or other conditions) which dictate calcination at above 700° F., this should preferably be done prior to addition of Group VIII metal. Alternatively, if the catalyst is to be calcined at above 700° F. after the Group VIII metal is added, then steps b and c infra of hydrogen activation should be carried out at temperature of 1200° F. or higher.

A preferred composition may contain 15.5% of NiO, 1.8% K$_2$O, and 74.1% gamma Al$_2$O$_3$. Another preferred composition may contain 7.5% of NiO, 1% K$_2$O, and 91.5% gamma Al$_2$O$_3$-percentages in this paragraph being on a weight basis.

The catalyst composition of this invention may be prepared by impregnating the support with solutions of metals of Groups VIII and I A. Typically for example it may be found that the catalyst may be prepared by:

(a) impregnating the support sequentially with several solutions each containing one or more of the metals and thereafter drying and calcining;

(b) impregnating the support with one or more solutions containing less than all of the metals (i.e. species or amount), drying and/or calcining, thereafter impregnating the support with the remaining metals, and drying and/or calcining; etc.

In the preferred embodiment, the catalyst composition may be in the form of pellets, cylinders, or randomly shaped particles; a typical catalyst composition may be in the form of cylinders, of diameter 1–15 mm, say 1.5 mm and height 1–15 mm, say 8–10 mm.

It is a feature of the preferred catalyst of this invention that it be activated prior to use (eg in steam dealkylation).

The catalyst may be activated by maintaining it in hydrogen atmosphere at 650° F.–1400° F., preferably 650° F.–1000° F., say 900° F. for 2–30 hours, preferably 2–20 hours, say 14 hours thereby forming a hydrogen-treated catalyst.

Preferably activation may be carried out by the process which comprises (a) heating the unactivated catalyst at a rate of 10–500, say 200° F./hr to a temperature of 650° F.–1400° F., say 900° F. in a hydrogen atmosphere;

(b) maintaining the heated unactivated catalyst in a hydrogen atmosphere at 650° F.–1400° F., preferably 650° F.–1000° F., say 900° F., for 2–30 hours, preferably 2–20, say 14 hours, thereby forming a hydrogen-treated catalyst;

(c) preferably maintaining the hydrogen-treated catalyst in a steam-hydrogen atmosphere at 650° F.–1400°

F., preferably 650° F.-1000° F., say 900° F., for 2-20 hours, preferably 2-15, say 2 hours, thereby forming a steamed hydrogen-treated catalyst; and (d) preferably cooling the steamed hydrogen-treated catalyst to 650° F.-850° F. in a steam-containing, eg steam or steam-hydrogen, atmosphere thereby forming an activated catalyst.

Activation of the steam dealkylation catalyst of this invention may preferably be carried out after the catalyst is in place in the reaction vessel. The vessel may be filled with catalyst composition to a bed bulk density of 40-80 pcf, say 46 pcf. In the first portion of the activation operation, the catalyst composition is heated at a rate of 10° F.-500° F., preferably 50° F.-250° F. say 200° F. per hour. Heating is continued at 650° F.-1400° F., preferably 650° F.-1000° F., say 900° F. in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components including oxygen.

The gas may contain (in addition to hydrogen) helium or more preferably light paraffins such as methane, ethane, propane, etc. Hydrogen may be present typically in amount of 30 mole %-100 mole %, preferably 80 mole %-100 mole %, say 100 mole %; i.e. the preferred embodiment may be that in which the gas consists essentially of hydrogen.

In the second or holding step, preferably the catalyst composition may be maintained for 2-30 hours, typically 2-20 hours, say 14 hours in a stream of flowing hydrogen typically flowing at a space velocity VHSV (STP) greater than about 3, more preferably greater than 100, say 100-500, typically 300.

When activation is carried out at atmospheric pressure, as in the preferred embodiment, the partial pressure of hydrogen may be at least about 9 psia (400 mm Hg), preferably 12-15 psia, say 15 psia (760 mm Hg).

In the preferred third portion of the activation cycle, the hydrogen-treated catalyst may be maintained at 650°-1400° F., preferably 650°-1000° F., say 900° F. (most preferably at about the same temperature as that employed in the second portion) in a flowing stream of hydrogen and steam. This steam may contain 15-50 mole %, preferably 20-40 mole %, say 30 mole % of hydrogen, 50-85 mole %, preferably 60-80 mole %, say 70 mole % of steam, and 0-10 mole %, preferably 0-5 mole %, say about 0 mole % of inert gas such as helium, nitrogen, or light paraffins. Preferably the gas may consist essentially of hydrogen and steam in molar ratio of 0.2-1, typically 0.25-0.67, say 0.42.

When activation is carried out at atmospheric pressure, as in the preferred embodiment, the partial pressure of hydrogen may be 100-380, preferably 150-300, say 240 mm Hg; and the partial pressure of steam may be 380-660, preferably 460-610, say 520 mm Hg.

The third portion of the activation procedure may be carried out for 2-10 hours, preferably 2-5 hours, say 2 hours in a steam of flowing gas at a space velocity VHSV (STP) greater than about 1.5, preferably greater than 50, say 50-250, typically 150.

Post activation cooling is typically carried out by maintaining the activated catalyst in a stream of flowing steam for 1-10 hours, preferably 1-5 hours, say 2 hours at the temperature is lowered to the steam dealkylation temperature of 600° F.-950° F., preferably 650° F.-900° F., say 800° F. Preferably steam is present during post activation in amount of 50-100 mole %, typically 80-100 mole %, say about 100 mole % of the flowing stream.

It is a feature of the catalyst of this invention that, in the activated form, it is characterized by the presence of Group VIII metal, preferably nickel, in the form of metal. The catalyst as prepared contains Group VIII metal as oxide; and this oxide must be reduced at least in part prior to use as catalyst. Reduction, during activation, is sufficient to reduce at least a portion of the Group VIII metal oxide to metal. The activated or reduced catalyst may normally contain eg 15-100 mole percent, preferably 50-100 mole percent, say 70 mole percent of the Group VIII metal in the form of metal and the remainder in a combined form such as the oxide or aluminate.

Thus the activated or reduced catalyst may be characterized by the formula:

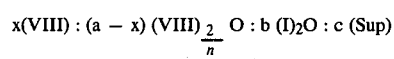

wherein the symbols a, b, and e are as noted supra and x is 0.0003-0.75, preferably 0.001-0.38, say 0.14. This is equivalent to saying that activation has reduced a portion of the oxide of the Group VIII metal to the free metal; and the free metal (expressed as oxide) is present in mole percent of preferably 50%-100%, say 70% of the total of metal plus oxide; (it will be apparent that x is less than a).

In the preferred embodiment, the activated catalyst may be

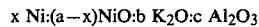

where x is 0.01-0.54, preferably 0.04-0.27, say 0.14 and the other values are as above. In this instance, this is equivalent to saying that of the total nickel content of metal and oxide, 15%-100%, preferably 50%-100%, say 70% by weight is in the form of nickel metal.

It is a feature of the catalysts of this invention that measurement of the surface area of the free Group VIII metal present reveals that the process of this invention may be carried out to give yields above about 95%, when that surface area is greater than about 8 square meters per gram of total activated catalyst composition. Preferably the surface area may be 8-24, say 8 square meters per gram as determined by the nickel metal content (by intensity of the diffraction line) and metallic nickel weight average crystal size.

Steam dealkylation of the hydrocarbon charge may be carried out by passing the charge at 600° F.-950° F., preferably 650°-900° F. and pressure of 0-400 psig, preferably 0-200 psig, say 0 psig together with steam in amount of 2-25 moles, preferably 3-15 moles, say 6 moles per mole of hydrocarbon charge (corresponding to 100-125%, preferably 150%-750%, say 300% of the stoichiometric quantity) to a reaction zone. In commercial practice it may be desirable to operate at e.g. 125 psig.

During steam dealkylation at these conditions, alkyl groups are removed from the charge alkylaromatic hydrocarbons to form product hydrocarbons bearing lesser numbers of alkyl groups on the aromatic nuclei. When the charge hydrocabon contains ethylbenzenes for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain benzene. In addition, the product hydrocarbon stream may contain the paraffin derived from the charge eg ethane or methane; and it may contain unreacted charge hydrocarbons in addition to other by-products.

Product hydrocarbon may be withdrawn from the reaction vessel and condensed. The liquid condensation may represent a recovery of 50-94 mole %, preferably 70-94 mole %, say 85 mole % of the hydrocarbon charged.

In the case of a pure toluene charge for example, the product (moles per 100 moles of charge toluene) may contain the following:

TABLE

| Component | Broad | Preferred | Typical |
|---|---|---|---|
| Unreacted Toluene | 4-79 | 13-70 | 37 |
| benzene | 20-61 | 30-60 | 55 |
| hydrogen | 60-183 | 90-180 | 165 |
| $CO_2$ | 20-61 | 30-60 | 55 |

In practice of the process of this invention according to the one embodiment, the reaction is carried out on a short cycle basis; i.e. the reaction proper (with a charge of steam and hydrocarbon) is carried out for 0.5-3.0 minutes, preferably 0.5-2.0 minutes, say 1 minute and then the catalyst is regenerated by shutting off the flow of hydrocarbon (and contacting it with the hydrocarbon-free steam) for 0.5-15 minutes, preferably 1-8 minutes, say 3 minutes. The ratio of regeneration time to reaction time may be 1-5, preferably 2-4, say 3.

It is found during practice of the process of this invention that it is possible, particularly when using the short cycle technique, to achieve improved catalyst activity. For example the toluene conversion (in terms of mole percent of toluene charge converted) may be 50%-90%, typically 65%-95%, say 70% in the preferred embodiment in contrast to comparable processes wherein the corresponding values are less than 45%.

It is also a feature of the process of this invention in its preferred embodiment, particularly when using the short cycle technique, that it permits attainment of benzene yield (in terms of mole percent of the charge toluene converted to benzene) which may be 40%-60%, typically 50-55%, say 54%. Comparable processes may achieve benzene yields of less than about 35% and commonly 10%-20%.

The novel process permits attainment of these conversions and yields with a high selectivity. The selectivity (in terms of moles of benzene recovered in the products per 100 moles of toluene converted) may approach 95% and may commonly be 65%-90%.

It is also a feature of this invention that the catalyst is found to be characterized by increased steam stability and durability. Although it may be found that the crush strength (in pounds) of the alumina support may decrease by as much as 50% during steaming, it is unexpectedly found that the crush strength of the catalyst of this invention (with an alumina support) is essentially equal to the crush strength of fresh alumina support; and this crush strength (and the surface area of the catalyst) may unexpectedly remain essentially constant or increase during steaming.

It is also a feature of the catalyst of this invention that it is possible to achieve these desirably improved novel results by use of a catalyst composition which unexpectedly contains such a low concentration of nickel. Typically the catalyst composition of this invention contains about 6%-40%, preferably 6%-20%, say 15% by weight of nickel metal. The preferred prior art catalysts typically contain 15%-80%, preferably 30%-70%, say 63% nickel metal. The ability to obtain substantial results by use of a catalyst containing one-third or less nickel permits substantial savings in capital costs in terms of cost of nickel.

EXAMPLES I-IV

In this experimental example which represents practice of the process of this invention the support used was American Cyanamid Aero 100 Brand, one-sixteenth inch, extrudates of gamma alumina.

Prior to use, the alumina is charged into a stainless steel tubular reactor and heated to 1110° F. for 12 hours while passing 64 g/hr of water and 8.0 cu. ft/hr of air through the bed. The steamed alumina is then calcined for two hours at 1000° F. The surface area of the alumina is reduced by this treatment from an initial value of 231 $m^2/g$ to a final value of 192 $m^2/g$.

166 parts of steam sintered alumina support is placed within a container and chilled in an ice bath. 257 parts of aqueous solution containing 148.5 parts of nickelous nitrate hexahydrate Ni $(NO_3)_2.6H_2O$ and 8.6 parts of potassium nitrate $KNO_3$ is poured over the chilled support. The resulting material is dried by heating overnight at 200° F. and then by heating for two hours at 300° F. The metal salts are decomposed by heating in air at 700° F. for 2 hours; and the catalyst is calcined in a muffle furnace at 700° F. for two hours. The so-prepared experimental catalyst contains 15.5% NiO (12.5% Ni), 1.8% $K_2O$, and 74.1% $Al_2O_3$. This catalyst had a nominal (or intended) composition of 15% NiO-2% $K_2O$-83% $Al_2O_3$.

The catalyst, 100 cc or 71 g, is charged into a fixed bed tubular reactor (one inch i.d. and 18 inches long) —it is centered in the reactor by 0.25 inch Berl saddles. The reactor is operated in a vertical downflow mode. Steam is formed by passing water to a preheater; and toluene is admitted to the steam line. The mixture is passed through a second preheater before entering the reactor.

The upper part of the reactor, which is packed with Berl saddles also serves as a preheater to bring the feed mixture to desired reaction temperature. Reactor operation is at atmospheric pressure; and the effluent is passed through a cold water condenser and then into a receiver which is cooled to ice-water temperature.

The liquid condensate is separated into two layers and the hydrocarbon samples analyzed by gas chromatography. The off-gas is measured in a wet test meter and analyzed by mass spectroscopy.

In the course of operation, the catalyst is activated by contact with flowing hydrogen (one liter STP per minute) as heating it continued at a rate of 200° F./hr to a final temperature of 900° F. followed by holding at 900° F. for 14 hours with flowing hydrogen (0.5 l/min) and for 2 hours with steam (36 g/hr) and hydrogen (0.5 l/min). At the end of activation, hydrogen flow is stopped, and the reactor is cooled to 660° F.

In operation, a mixture of steam and toluene is charged at constant rate; and the run is considered started when hydrocarbon appears in the receiver. The run is carried out using short cycling i.e. a period of one minute of reaction charging toluene plus steam is followed by a period of 3 minutes of regeneration charging steam alone.

In this series of examples, each example was carried out over 45 minutes at selected temperatures; and the following were measured:

(a) temperature in °F.—average temperature in the bed;

(b) MHSV—hourly space velocity of toluene charge;

(c) Steam: toluene mol ratio—this like the MHSV being calculated on the basis of the total cut period of 45 minutes and includes both reaction and regeneration times;

(d) Carbon Balance—% of charge;

(e) Toluene conversion—mole % of the charge converted to products—based upon 100% carbon balance;

(f) Benzene yield—mole % of the charge converted to benzene—based upon 100% carbon balance;

(g) Benzene selectivity—moles of benzene recovered in the products per one hundred moles of toluene converted in the reaction.

TABLE

| | EXAMPLE | | | |
|---|---|---|---|---|
| | I | II | III | IV |
| Temp. °F. | 660 | 730 | 800 | 875 |
| Toluene MHSV | 0.32 | 0.27 | 0.27 | 0.29 |
| St: Tol mole ratio | 9.7 | 10.1 | 10.4 | 9.8 |
| Carbon Balance % charge | 93 | 104 | 110 | 101 |
| Tol. Conv. Mol. % charge | 39 | 54 | 76 | 84 |
| Benzene Yield Mol. % charge | 36 | 48 | 61 | 55 |
| Benzene Sel Mol. % | 93 | 89 | 80 | 65 |

From the above table it is apparent that the novel process of this invention permits steam dealkylation of toluene to give benzene product in high conversion, yield, and selectivity. In the preferred embodiment, operating at 800° F. for example, it is possible to attain a conversion of 76%, a selectivity of 80%, and a yield of 61%.

In prior techniques at comparable temperatures, the yield may be only about 24%-25% i.e. the number of moles of benzene produced per mole of charge toluene may be less than half that obtained when following the process of the instant invention.

EXAMPLES V-XVII

In this series of steady flow examples, the same catalyst was used as for Examples I-IV. It was activated by contact with flowing hydrogen (one liter per minute) as it is heated at a rate of 200° F./hr to a final temperature of 900° F., followed by holding at 900° F. for 14 hours (with a flow of hydrogen of 0.5 liters per minute)—followed by an additional 2 hours in the presence of flowing steam (36 grams per hour) and hydrogen (0.5 liters per minute). At the end of activation, the hydrogen flow is stopped; and the reactor is brought to the desired temperature of 800° F. (Example V is run at 785° F.).

In each Example, the product is collected for a fixed period—Example V—5 minutes, Example VI—15 minutes, Example VII—40 minutes, Examples VIII-XVII—60 minutes.

At the end of Example XII, the reactor is flushed with hydrogen and left under hydrogen (75-90 psig) at 800° F. for about 16 hours.

TABLE

| Example | Toluene WHSV | St: Tol Mol. Ratio | Tol. Conv. Mol % Chg | Benz. Yield Mol % Chg |
|---|---|---|---|---|
| V | 1.19 | 1.5 | 72 | 51 |
| VI | 1.31 | 2.6 | 60 | 59 |
| VII | 1.29 | 2.4 | 51 | 47 |
| VIII | 1.29 | 2.5 | 30 | 28 |
| IX | 1.30 | 2.0 | 31 | 29 |
| X | 1.29 | 2.0 | 30 | 27 |
| XI | 1.29 | 2.0 | 30 | 21 |
| XII | 1.29 | 2.1 | 29 | 27 |
| XIII | 1.29 | 2.1 | 42 | 37 |
| XIV | 1.28 | 2.0 | 38 | 35 |
| XV | 0.45 | 5.7 | 41 | 37 |
| XVI | 1.28 | 2.1 | 36 | 33 |
| XVII | 1.28 | 2.0 | 33 | 28 |

From the above Table, it is apparent that use of a (nominal) 15 $NiO$-2$K_2O$-83 $Al_2O_3$ catalyst during continuous flow operation permits initial conversion of 72 mol % of the toluene to give a benzene yield of 51 mol %. During continuous flow operation, the catalyst activity decreases to give a toluene conversion of 51% after one hour and of 29%-31% after 6 hours. Standing overnight in hydrogen (Ex XIII) temporarily regenerates the catalyst, but after 4 hours the catalyst activity declines to give the equilibrium benzene yield of −28 mol %.

EXAMPLES XVIII-XXIII

In this series of Examples, the same system was used as for Examples V-XVII. The cut period for each example is 60 minutes and the temperature is 800° F. Each example is run on a short cycle basis in which reaction occurs for one minute during which toluene and steam are passed through the bed followed by regeneration for 3 minutes during which only steam is passed through the bed.

At the end of Example XVIII, the reactor is flushed with hydrogen (75-90 psig) at 800° F. for 16 hours.

TABLE

| Example | Toluene WHSV | St: Tol Mol. Ratio | Tol. Conv. Mol % Chg | Bz Yield Mol % Chg |
|---|---|---|---|---|
| XVIII | 0.20 | 12.8 | 46 | 40 |
| XIX | 0.19 | 14.0 | 73 | 60 |
| XX | 0.21 | 11.8 | 70 | 55 |
| XXI | 0.15 | 16.8 | 70 | 58 |
| XXII | 0.21 | 11.8 | 69 | 55 |
| XXIII | 0.29 | 8.6 | 60 | 52 |

From the above Table, it is apparent that the effectiveness of short cycling is demonstrated by the immediate increase in benzene yield from 28% up to 40% and an increase in toluene conversion from 33% up to 46% after only one hour. Thereafter, the toluene conversion is maintained at a desirably high level of 60%-73% and the benzene yield is also desirably high at 52%-60%.

Results comparable to those set forth supra may be obtained by using the following catalyst systems:

| EXAMPLE | CATALYST (wt%) | | |
|---|---|---|---|
| XXIV | 15% $NiO$ | : 2% $K_2O$ | : 83% $Al_2O_3$ |
| XXV | 7.5% $NiO$ | : 1% $K_2O$ | : 91.5% $Al_2O_3$ |
| XXVI | 15% $NiO$ | : 2% $Na_2O$ | : 83% $Al_2O_3$ |
| XXVII | 30% $NiO$ | : 3% $K_2O$ | : 67% $Al_2O_3$ |
| XXVIII | 15% $CoO$ | : 2% $K_2O$ | : 83% $Al_2O_3$ |
| XXIX | 7% $NiO$ | : 2% $Na_2O$ | : 91% $SiO_2$ |
| XXX | 5% $NiO$ | : 1% $K_2O$ | : 94% $SiO_2$ |
| XXXI | 1% $Pt_2O$ | : 2% $K_2O$ | : 97% $Al_2O_3$ |

| EXAMPLE | CATALYST (wt%) | | |
|---|---|---|---|
| XXXII | 20% CoO | : 2% K$_2$O | : 78% Al$_2$O$_3$ |

Although this invention has been illustrated by reference to specific embodiments, it will be apparent to those skilled in the art that various changes and modifications may be made which clearly fall within the scope of the invention.

We claim:

1. The method of activating a supported catalyst containing oxides of a Group VIII metal and of a Group I A metal which comprises
    heating said catalyst at a rate of 10°–500° F./hr to a temperature of 650° F.–1400° F. in a hydrogen atmosphere;
    maintaining said heated catalyst in a hydrogen atmosphere at 650° F.–1400° F. for 2–30 hours thereby forming a hydrogen-treated catalyst; and
    maintaining the hydrogen-treated catalyst in a steam-hydrogen atmosphere at 650° F.–1400° F. for 2–20 hours thereby forming a steamed hydrogen-treated catalyst.

2. The method of activating a catalyst as claimed in claim 1 wherein said steamed hydrogen-treated catalyst is cooled to 600° F.–950° F. in a steam-containing atmosphere.

3. The method of activating a catalyst as claimed in claim 1 wherein said catalyst is $$a\,(VIII)_{\frac{2}{n}}O : b\,I_2O : c\,(Supp)$$

wherein a is 0.002–0.75, b is 0.00003–0.17, c is 0.15–2.49 VIII is a metal of Group VIII of the Periodic Table, n is the valence of VIII, I is a metal of Group I A of the Periodic Table, and Supp is support.

4. The method of activating a catalyst as claimed in claim 1 wherein said catalyst is $$a\,NiO : b\,K_2O : c\,Al_2O_3$$

wherein a is 0.08–0.54, b is 0.01–0.05, and c is 0.75–0.91.

5. An activated supported catalyst composition comprising a catalyst support and distributed thereon oxides of (i) a Group VIII metal and (ii) a Group I A metal wherein said catalyst has been initially activated by the process which comprises
    (i) heating the unactivated catalyst at a rate of 10°–500° F./hr to a temperature of 650° F.–1400° F. in a hydrogen atmosphere;
    (ii) maintaining the heated unactivated catalyst in a hydrogen atmosphere at 650° F.–1400° F. for 2–30 hours thereby forming a hydrogen-treated catalyst;
    (iii) maintaining the hydrogen-treated catalyst in a steam-hydrogen atmosphere at 650° F.–1400° F. for 2–30 hours thereby forming a steamed, hydrogen-treated catalyst; and
    (iv) cooling said steamed, hydrogen-treated catalyst to 650° F.–850° F. in a steam-containing atmosphere thereby forming an activated catalyst.

6. An activated supported catalyst as claimed in claim 5 wherein said Group VIII metal is nickel or cobalt.

7. An activated supported catalyst as claimed in claim 5 wherein said Group VIII metal is nickel.

8. An activated supported catalyst as claimed in claim 5 wherein said Group I A metal is potassium.

9. An activated supported catalyst as claimed in claim 5 wherein said catalyst is $$a\,(VIII)_{\frac{2}{n}}O : b\,I_2O : c\,(Supp)$$

wherein a is 0.002–0.75, b is 0.00003–0.17, c is 0.15–2.49 VIII is a metal of Group VIII of the periodic table, n is the valence of VIII, I is a metal of Group I A of the periodic table, and Supp is support.

10. An activated supported catalyst as claimed in claim 5 wherein said catalyst is $$a\,NiO : b\,K_2O : c\,Al_2O_3$$

wherein a is 0.08–0.54, b is 0.01–0.05, and c is 0.75–0.91.

11. An activated supported catalyst as claimed in claim 5 wherein said catalyst is $$0.20NiO : 0.02K_2O : 0.81Al_2O_3.$$

12. The method of activating a supported catalyst $$a\,NiO : b\,K_2O : c\,Al_2O_3$$

wherein a is 0.02–0.75, b is 0.00003–0.17, and c is 0.15–2.49 which comprises
    heating said catalyst at a rate of 10°–500° F./hr to a temperature of 650° F.–1400° F. in a hydrogen atmosphere;
    maintaining said heated catalyst in a hydrogen atmosphere at 650° F.–1400° F. for 2–30 hours thereby forming a hydrogen-treated catalyst; and
    maintaining the hydrogen-created catalyst in a steam-hydrogen atmosphere at 650° F.–1400° F. for 2–20 hours thereby forming a steamed hydrogen-treated catalyst.

* * * * *